United States Patent [19]

Fülberth et al.

[11] 3,931,404

[45] Jan. 6, 1976

[54] HIGH DOSAGE ORALLY ADMINISTRABLE CEPHALOSPORIN ANTIBIOTIC PREPARATIONS

[75] Inventors: Werner Fülberth, Kelkheim, Taunus; Dietrich Hiller, Wiesbaden; Alfred Müller, Ehlhalten, Taunus; Gerhard Ross, Liederbach, Taunus, all of Germany

[73] Assignee: Hoechst Aktiengesellschaft, Frankfurt am Main, Germany

[22] Filed: Dec. 4, 1973

[21] Appl. No.: 421,605

[30] Foreign Application Priority Data
Dec. 6, 1972  Germany............................. 2259646

[52] U.S. Cl. .............................................. 424/246
[51] Int. Cl.² ......................................... A61K 31/54
[58] Field of Search ..................................... 424/246

[56] References Cited
UNITED STATES PATENTS

| | | | |
|---|---|---|---|
| 3,573,294 | 3/1971 | Long et al............................ | 424/246 |
| 3,624,225 | 11/1971 | O'Callaghan ....................... | 424/246 |

*Primary Examiner*—Stanley J. Friedman
*Attorney, Agent, or Firm*—Curtis, Morris & Safford

[57] ABSTRACT

High-dosage, orally administrable antibiotic preparations containing an antibiotic agent of the cephalosporin type and 5 to 15 % of a mixture of auxiliary agents, and process for preparing them.

7 Claims, No Drawings

HIGH DOSAGE ORALLY ADMINISTRABLE CEPHALOSPORIN ANTIBIOTIC PREPARATIONS

The present invention relates to high dosage antibiotic tablets, which are small in relation to the dose of active substance, of cephalosporins to be administered orally, for example cephalexin and cephaloglycin, and to a process for preparing them.

In oral therapy with antibiotics, higher doses are used in increasing degree in the treatment of infections in order to obtain rapidly sufficiently high levels of the drug in the blood of the patient.

It is not seldom that the antibiotic agent is administered in single doses of up to several grams.

Therefore, it is necessary to develop orally administrable drug forms of these antibiotics which have as high a content of antibiotic agent as possible.

Since in most cases antibiotics have a very disagreeable bitter taste, drug forms must be chosen which can be swallowed whole without difficulty. They may also be additionally provided with a coating.

After ingestion, these tablets must rapidly disintegrate in the digestive tract and release the active substance for resorption.

The swallowability of higher-dose tablets can be facilitated by giving them a certain form (for example oval or oblong form).

Dosage unit forms of drugs which, as regards their size, can still be swallowed have maximum weights of about 0.25 to 3 g, depending on the bulk volume of the tablet mixture.

In order to obtain tablets with optimum properties and to ensure their preparation on modern high speed machines, the active substances, depending on their flow and compressing behavior, are normally combined according to the state of the art with auxiliary agents, the quantity of which is often higher than that of the active substance. In normal cases, quantities of auxiliary agents of 30% and more are necessary to impart on a medicinal substance good properties for tablet formation and to ensure good quality of the drug dosage form.

As auxiliary agents, there may be mentioned, for example:
diluents such as lactose, sugar,
binders such as starch, cellulose derivatives,
disintegrators such as starch, ultraamylopectin,
lubricants such as talc and magnesium stearate.

When formulating tablet mixtures, suitable auxiliary agents must be selected and used in such quantities that flowable mixtures or granulates are obtained which permit efficient production of tablets that have optimum properties with regard to disintegration, release of active substance, hardness, breakability and appearance.

With tablets containing a high dose of active substance, it is particularly important to keep the quantity of auxiliary substances low in order to avoid the tablets becoming too large. On the other hand, the tablets must show sufficient properties, in particular good disintegration and release of the active ingredient.

Cephalosporins and their derivatives, in particular cephalexin and cephaloglycin, have very poor flow characteristics. Even in a bottle, they tend to agglomeration and clot-formation owing to electrostatic charging, so that the expert can obtain mixtures or granulations which can be processed into tablets only by adding large amounts of auxiliary agents.

On the other hand, economical production of tablets on machines with high capacity requires mixtures and granulations containing the active ingredient which show a sufficient flow behavior also at a high speed of the tablet machine. Large matrices in oblong form must be filled uniformly to secure equal dosages. Capping and any other mechanical damage which occurs, especially with high compressing speeds, must be avoided. These disadvantages are overcome by the addition of high amounts of well flowing auxiliary agents.

Thus, an expert could not foresee that an advantageous, economical production of such tablets, i.e. tablets having a high content of active ingredient and a low content of auxiliary agents, would be possible.

Now, we have found a process for the economical preparation of high-dosage tablets of as small a size as possible with an antibiotic powder having poor flow characteristics and belonging to the cephalosporin type, wherein about only 5 to 15% of a mixture of auxiliary agents, for example a mixture of starch, microcrystalline cellulose, ultraamylopectin, talc and/or magnesium stearate is added to the said active ingredients and the resulting mixture is granulated and compressed into tablets. If desired, these tablets may be provided with a suitable coating.

As antibiotic agents of the cephalosporin type, there are used in particular cephalexin and cephaloglycin.

The proportions of the above-mentioned active ingredients and auxiliary agents may be as follows:

| | |
|---|---|
| cephalosporin derivative | 85 – 95 % |
| crystalline cellulose | 10 – 2.5 % |
| ultraamylopectin | 3 – 1.5 % |
| magnesium stearate | 2 – 1 % |
| or | |
| cephalosporin derivative | 85 – 93 % |
| lactose | 8 – 4 % |
| ultraamylopectin | 5 – 2 % |
| magnesium stearate | 2 – 1 % |
| or | |
| cephalosporin derivative | 85 – 95.0 % |
| starch or starch derivative | 8 – 2.6 % |
| talc | 5 – 2.0 % |
| magnesium stearate | 2 – 0.4 % |

Crystalline cellulose is a product obtained upon treatment of cellulose-containing materials.

Lactose serves as a tablet filler material.

Starch and starch derivatives are known as disintegrators.

Ultraamylopectin is a starch product which is obtained by the reaction of sodium alcoholate and halogenated fatty acid and starch. Owing to its swelling power it is used as tablet disintegrating agent.

Magnesium stearate and talc have been described in various pharmacopoeas as lubricants and antisticking agents.

If necessary, other auxiliary agents usually employed in the production of tablets may be added.

Of course, the mixtures of the invention may also be compressed into smaller tablets with lower dosage (for example, for children) or into larger tablets with higher dosage (for example, for vaginal administration or for animals).

The mixtures of the above-mentioned composition obtained after granulation are free flowing and can be processed on high-speed machines into high quality tablets at a rate of 3000 tablets per minute.

Depending on the solubility of the active ingredient in water, the tablets show in water or in artificial gastric juice of 37° C a disintegration time of a few minutes to 6 minutes at maximum.

For protection against environmental influences, for example humidity, light, etc. and in order to cover the taste, the tablets so produced may be provided with a film or dragée coating (if desired flavored) according to the processes usual in the pharmaceutic industry.

The following Examples illustrate the invention:

EXAMPLE 1:

Tablets of 500 mg or 1000 mg of cephalexin each.

| Composition: | |
|---|---|
| cephalexin including overdosage | 90.6 % |
| crystalline cellulose | 6.4 % |
| ultraamylopectin | 2.1 % |
| magnesium stearate | 0.9 % |
| | 100.0 % |

Preparation:

A mixture of the above-specified substances was prepared in a rapid mixer and a granulation having a grain size of between 2.0 and 0.3 mm was prepared.

The granulated mixture was compressed on a rotary tablet machine at a speed of 2000 to 3000 tablets/minute into convex oblong tablets with score.

The tablets were found to disintegrate in artificial gastric juice of 37° C within 3 minutes at maximum.

If desired, these dosage forms can be provided with a flavored film or dragée coating.

EXAMPLE 2:

Tablets of 500 mg or 1000 mg of cephalexin.

| Composition: | |
|---|---|
| cephalexin including overdosage | 90.7 % |
| lactose | 6.3 % |
| ultraamylopectin | 2.1 % |
| magnesium stearate | 0.9 % |
| | 100.0 % |

Preparation:

A mixture was prepared from the above-mentioned substances in a rapid mixer and a granulation was prepared having a grain size of between 2.0 and 0.3 mm.

The granulated mixture was compressed on a rotary tablet machine into convex oblong tablets with score at a speed of about 2000 to 3000 tablets per minute.

The tablets were found to disintegrate in artificial gastric juice of 37° C within 5 to 6 minutes at maximum.

If desired, these dosage forms can be provided with an optionally flavored film or dragée coating.

EXAMPLE 3:

Tablets of 500 mg or 1000 mg of cephalexin.

| Composition: | |
|---|---|
| cephalexin including overdosage | 93.0 % |
| maize starch | 3.5 % |
| talc | 3.0 % |
| magnesium stearate | 0.5 % |
| | 100.0 % |

Preparation:

A mixture was prepared from the above-mentioned substances in a rapid mixer and a granulation was prepared having a grain size of between 2.0 and 0.3 mm.

The granulated mixture was compressed on a rotary tablet machine into convex oblong tablets with score at a rate of about 2000 to 3000 tablets per minute.

The tablets were found to disintegrate in artificial gastric juice of 37° C within 5 to 6 minutes at maximum.

If desired, these dosage forms can be provided with an optionally flavored film or dragée coating.

We claim:

1. An antibiotic preparation in compressed tablet form consisting essentially of cephalexin or cephaloglycin and from 5 to 15 percent, by weight of said preparation, of pharmaceutical excipients selected from the group consisting of starch, crystalline cellulose, lactose, ultraamylopectin, talc, and magnesium stearate.

2. A preparation as in claim 1 consisting essentially of
85 to 95 percent of a cephalosporin antibiotic,
10 to 2.5 percent of crystalline cellulose,
3 to 1.5 percent of ultraamylopectin, and
2 to 1 percent of magnesium stearate.

3. A preparation as in claim 1 consisting essentially of
85 to 93 percent of a cephalosporin antibiotic,
8 to 4 percent of lactose,
5 to 2 percent of ultraamylopectin, and
2 to 1 percent of magnesium stearate.

4. A preparation as in claim 1 consisting essentially of
85 to 95 percent of a cephalosporin antibiotic,
8 to 2.6 percent of starch,
5 to 2 percent of talc, and
2 to 0.4 percent of magnesium stearate.

5. A preparation as in claim 1 wherein said cephalosporin antibiotic is cephalexin.

6. As a dosage unit form for oral administration, a compressed tablet comprising from 0.25 g to 3 g of the preparation as in claim 1.

7. The method of making a dosage unit form for oral administration which comprises compressing from 0.25 to 3 g of the preparation as in claim 1 into tablet form.

* * * * *